United States Patent
McDermott et al.

(10) Patent No.: US 6,312,462 B1
(45) Date of Patent: Nov. 6, 2001

(54) PROSTHESIS FOR ABDOMINAL AORTIC ANEURYSM REPAIR

(75) Inventors: John D. McDermott, Mesa; David Renzi, Scottsdale, both of AZ (US); Richard W. Layne, E. Palo Alto, CA (US); Christopher E. Banas, San Antonio, TX (US)

(73) Assignee: Impra, Inc., Tempe, AZ (US)

(*) Notice: Subject to any disclaimer, the term of this patent is extended or adjusted under 35 U.S.C. 154(b) by 0 days.

(21) Appl. No.: 09/401,436

(22) Filed: Sep. 22, 1999

(51) Int. Cl.[7] .................................................. A61F 2/06
(52) U.S. Cl. ......................................... 623/1.25; 623/1.28
(58) Field of Search ................................ 623/1.24, 1.25, 623/1.27, 1.29, 1.35, 1.44, 1.49

(56) References Cited

U.S. PATENT DOCUMENTS

| | | |
|---|---|---|
| 3,435,824 | 4/1969 | Gamponia . |
| 5,100,429 | 3/1992 | Sinofsky et al. . |
| 5,108,370 | 4/1992 | Walinksy . |
| 5,151,105 * | 9/1992 | Kwan-Gett ........................... 623/1.23 |
| 5,156,620 * | 10/1992 | Pigott ................................... 623/1.23 |
| 5,275,622 | 1/1994 | Lazarus et al. . |
| 5,328,471 | 7/1994 | Slepian . |
| 5,330,528 * | 7/1994 | Lazim ................................... 623/1.23 |
| 5,360,443 | 11/1994 | Barone et al. . |
| 5,423,851 * | 6/1995 | Samuels ................................ 606/198 |
| 5,441,485 | 8/1995 | Peters . |
| 5,489,295 | 2/1996 | Piplani et al. . |
| 5,545,135 | 8/1996 | Iacob et al. . |
| 5,554,180 * | 9/1996 | Turk ...................................... 623/1.25 |
| 5,607,468 | 3/1997 | Rogers et al. . |
| 5,613,948 | 3/1997 | Avellanet . |
| 5,665,117 | 9/1997 | Rhodes . |
| 5,693,088 * | 12/1997 | Lazarus ................................. 623/1.35 |
| 5,800,512 * | 9/1998 | Lentz et al. .......................... 623/1.32 |
| 5,871,537 | 2/1999 | Holman et al. . |
| 6,036,724 * | 3/2000 | Lentz et al. .......................... 623/1.32 |
| 6,045,496 * | 4/2000 | Pacella et al. ........................ 600/16 |
| 6,053,939 * | 4/2000 | Okuda et al. ......................... 623/1.23 |

FOREIGN PATENT DOCUMENTS

| | | |
|---|---|---|
| WO 93/05730 | 4/1993 | (WO) . |
| WO 97/03717 | 2/1997 | (WO) . |
| WO 97/09008 | 3/1997 | (WO) . |
| WO 99/39662 | 8/1999 | (WO) . |
| WO 00/01439 | 1/2000 | (WO) . |

* cited by examiner

Primary Examiner—David H. Willse
Assistant Examiner—Suzette J. Jackson
(74) Attorney, Agent, or Firm—Morrison & Foerster; Todd W. Wight

(57) ABSTRACT

The device of the present invention comprises a bifurcated graft fabricated from expanded PTFE (ePTFE). The inventive device is double walled so that following insertion into an aneurysm, fluid can be injected between the walls to expand the device thereby opening the inner tubular graft for receiving blood flow and locking the device into place in the aorta. The injected fluid may polymerize so that the device is permanently held in its expanded form. One embodiment of the device is fabricated with pockets or channels. After the device is delivered and expanded additional stiffening struts can be inserted into these pockets. In this way the basic device can be furled and tightly compressed for delivery (something not possible with a stent containing device). After the device is expanded, a stent-like structure can be inserted endovascularly giving the strength and resiliency of a stent-containing prosthesis.

10 Claims, 4 Drawing Sheets

PROSTHESIS FOR ABDOMINAL AORTIC ANEURYSM REPAIR

BACKGROUND OF THE INVENTION

1. Field of the Invention

The present application concerns medical devices for treatment of vascular disease and more particularly devices for treatment of abdominal aortic aneurysms.

2. Description of Related Art

Most of us are familiar with the problems of vascular blockage brought on by high fat diets, smoking and other risky behaviors. Generally fatty or other lesions block the vasculature requiring surgical replacement or unclogging (e.g., angioplasty) to restore blood flow. Such problems are common in the vasculature of the heart where blockage can result in "heart attacks". However, vascular narrowing and blockage is also common in the extremities (e.g., restriction of blood flow into a leg) as well as the vasculature supplying blood to the brain where blockage can result in a stroke.

While one does not normally think of these types of blockages occurring in the main artery (aorta) carrying blood away from the heart, other, possibly related, serious types of vessel disease do take place in the aortas. The abdominal aorta is the major artery carrying blood posteriorly from the heart and normally has a diameter two to two and one half centimeters in an adult. The aorta extends in a relatively straight path from the heart toward the groin and then bifurcates to supply blood to the legs. Perhaps because of its size and the volume of blood that moves through this vessel, fatty blockages and thromboses are not as common in this vessel. Rather, vascular disease often resulting from genetics, smoking and high blood pressure cause a weakening of the aorta's walls and a resulting distension.

Such distensions are known as an abdominal aortic aneurysms (AAA) when they occur in the aorta from the renal arteries down to the bifurcation to form the iliac arteries. At first an aneurysm is quite small but as the disease process continues, the aneurysm enlarges, the aorta wall thins and rupture ultimately results. When the aneurysm is less than 4.5 cm in diameter, danger of rupture is quite low. Even before the aneurysm grows large enough to pose a danger of rupture, however, it may cause other problems. The enlarged region often develops a thrombus that fills the distension so that blood flows only down the central region. Pieces of clot may break off from the thrombus and be carried away, resulting in blockages in the legs, lungs or even the brain.

The aneurysm generally does not remain small but enlarges at a rate of 0.3–0.5 cm per year. An 8 cm aneurysm has a 75% per year rupture risk. Needless to say rupture of such a major vessel is often fatal. About 15,000 people die each year in the United States from ruptured AAA's. If rupture occurs, 62% of the victims die before reaching a hospital. Of those surviving long enough to undergo surgery another 50% die. Even if the aneurysm is discovered before rupture, surgical repair is difficult and risky although surgery is 95% successful.

Traditional repair methods require full abdominal surgery with protracted recovery periods. Further, many weakened patients with heart disease or other maladies cannot be subjected to the rigor of such surgery. Therefore, many people are trying to develop an "endovascular" repair technique in which a prostheses is introduced into the aneurysm not by opening the patient's abdomen but by remote insertion of a femoral artery. After insertion the device is advanced to the aneurysm where it is deployed to repair the AAA. Clearly such a technique would significantly reduce patient complications and recovery times.

Much stenotic vascular disease is treated with stents—usually metallic meshes intended to force open a vessel. Simple stents are not ideal for AAA because the thrombus readily penetrates the open mesh of the stent and because blood passes through the mesh to place continued pressure on the aorta wall.

The other device common in vascular repair is a synthetic vascular graft made of expanded polytetrafluoroethylene (ePTFE). An advantage of these synthetic grafts is that they are extremely flexible and can be readily compressed to a very small size for endovascular insertion. However, bypassing generally requires suturing of the graft to the patient's vessels. This suturing is not possible with an endovascular insertion. Thus, if a synthetic graft is compressed and then inserted endovascularly into a AAA, it is unlikely that the graft will unfurl, anchor to the aorta and remain properly in place to repair the aneurysm.

Most current AAA devices combine a synthetic graft component with some type of a stent device. The graft is intended to exclude the thrombus and reinforce the aortal wall while the stent device ensures proper opening and anchoring of the device. Typical of such a device is that disclosed in U.S. Pat. No. 5,275,622 to Lazarus, which is a tubular collapsible graft, having a mechanical framework at its ends. Not only does the framework ensure proper opening of the tubular graft, it can also have barb-like anchors that fasten the graft to the walls of the vessel. This reference illustrates an unbranched prosthesis but U.S. Pat. No. 5,489,295 to Pilani et al. shows a bifurcated prosthesis comprising a tubular graft and a supporting stent structure along with a delivery system. U.S. Pat. No. 5,360,443 to Barone et al. discloses another version of an aneurysm repair prosthesis comprising a stent covered by a synthetic graft.

Successful endovascular AAA prostheses must meet a number of criteria. First, the graft wall material of the device must have sufficient strength to withstand the force of the blood flowing through the aorta. Second the device must become firmly and permanently anchored in the aorta. If the anchoring is inadequate, blood will leak around the graft and the device will ultimately fail. Third, the device must be sufficiently compressible to allow endovascular insertion. To some extent these factors work at cross purposes. If the graft material is thickened to ensure adequate strength, the device will have a larger compressed profile. If additional stents are added to improve the anchoring of the device and to enhance the strength of the device, the compressed profile will again be increased.

A number of prior art attempts have been made to make the graft material also act as a stent. U.S. Pat. No. 5,156,620 to Pigott discloses a semi-rigid tubular prosthesis with double walls. Following insertion a hardening polymer can be injected between the walls to permanently stiffen the device. U.S. Pat. No. 5,607,468 to Rogers et al. discloses an inflatable corrugated stent graft with an internal structure not unlike an air mattress. Such a device can be compressed for delivery and then expanded by injection of a liquid or gas. However, it appears that neither of these devices can be compressed to an extremely low profile. The bifurcated graft disclosed in U.S. Pat. No. 5,693,088 to Lazarus employs inflatable collars, primarily at the extremities of a bifurcated graft to ensure that the device is sealingly anchored in place. U.S. Pat. No. 5,665,117 to Rhodes combines a number of these features. A tubular graft is equipped with a stiffening stent and also surrounded by an inflatable balloon. Once the device is delivered to the aneurysm and the stent enlarged to hold open the tubular graft, the balloon can be inflated to occupy the peripheries of the aneurysm thereby anchoring the device in place.

SUMMARY OF THE INVENTION

In spite of the strides made in the prior art there is still a need for a AAA prosthesis with an extremely low compressed profile that can be expanded to permanently occupy an aneurysm. The device of the present invention comprises a bifurcated graft fabricated from expanded PTFE (ePTFE). This material is widely used for vascular grafts because of its flexibility, strength and biocompatibility. The inventive device is double walled so that following insertion into an aneurysm, fluid can be injected between the walls to expand the device, thereby expanding the outer graft to conform to the aorta and locking the device into place. It is also possible to inject a fluid that polymerizes so that the device is permanently locked into its expanded form. One embodiment of the device is fabricated with pockets or channels. After the device is delivered and expanded additional stiffening struts can be inserted into these pockets. In this way the basic device can be furled and tightly compressed for delivery (something not possible with a stent containing device). After the device is expanded, a stent structure can be inserted endovascularly giving the strength and resiliency of a stent-containing prosthesis.

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide a stent-free prosthesis for an abdominal aortic aneurysm that can be greatly compressed for insertion purposes and then inflated to repair the aneurysm.

Figure 1:
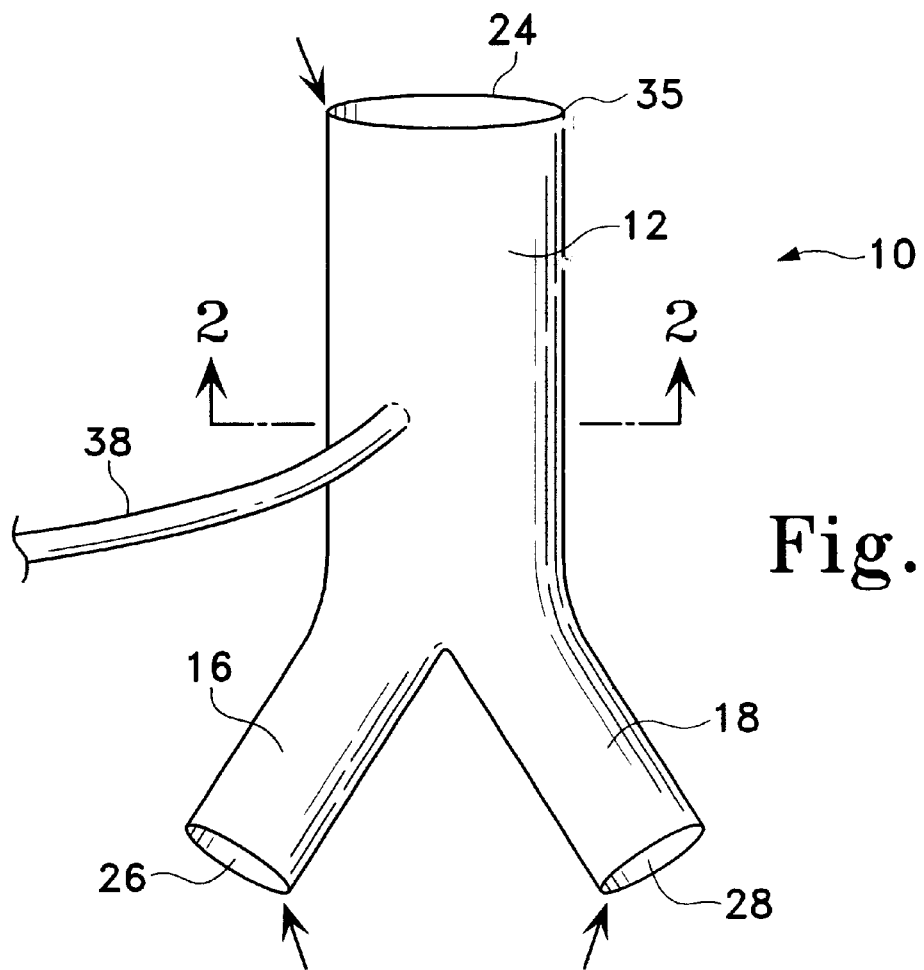
FIG. 1 is a perspective view of a first embodiment of the present invention.

FIG. 1 shows a perspective view of one embodiment of the present invention. The device 10 comprises a tubular body 12 having a central lumen 14. The tubular body 12 is bifurcated at one end into tubular iliac limbs 16, 18. The central lumen 14 is open at a distal end 24 of the device 10 and is in communication with lumens within the iliac limbs 16, 18. which are open at their proximal ends 26, 28. In general configuration the device 10 as described thus far is similar structurally to many prior art AAA prostheses although such devices normally also contain a stent. The entire structure is distinguished by being double-walled so that an inflating fluid can be injected between the walls.

Figure 2:
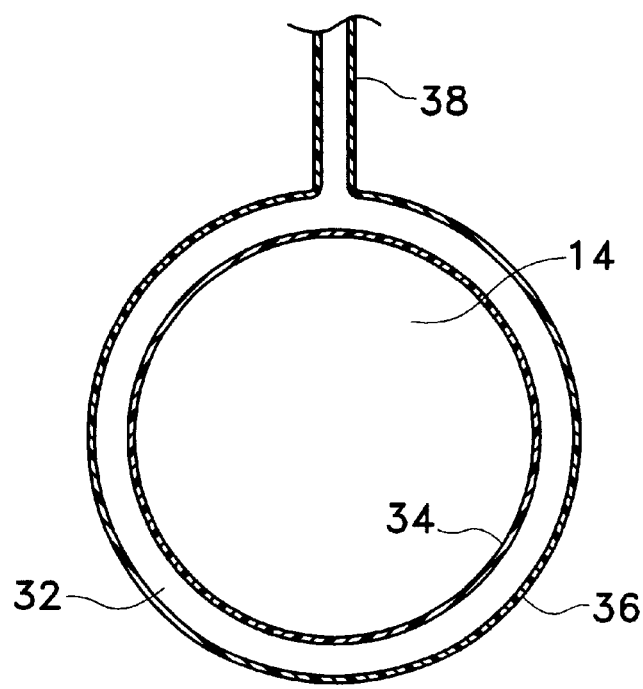
FIG. 2 is a cross-section of the device of FIG. 1 along lines 2—2.

As shown in FIG. 2 the walls of the main body 12 form an annular structure with an inflation space 32 between an inner wall 34 and an outer wall 36. In this embodiment of the device 10 the inner wall 34 and the outer wall 36 show a connection 35 only at the proximal and distal ends of the device 10 (also marked by "→" in FIG. 1). After the collapsed device 10 is delivered to the sight of an aneurysm, the inflation space 32 is filled by an inflation fluid which is delivered through an inflation conduit 38. Although it is possible to have the inflation conduit 38 permanently attached to the device 10, a preferred embodiment has the inflation conduit 38 removably attached through a valve mechanism (not shown) that allows the conduit 38 to be detached and/or reattached without leakage of the inflation fluid from either the inflation space 32 or the inflation conduit 38.

The inflation fluid can be as simple as saline, although a preferred inflation fluid is a gel or a liquid that forms a gel or even hardens after injection to render the device 10 permanently expanded. A wide range of gelling, hardening or polymerizable liquids are available and are well known to those of skill in the art. Various silicone rubbers, urethanes or other similar organic elastomers can be used although an ideal inflation fluid should be water because it is miscible and completely non-toxic. Various aqueous acrylamide monomer and similar solutions work well in the current invention because they polymerize in situ to produce strong and essentially non-toxic gels. However, the aqueous monomers, themselves, can be toxic. Various carbohydrate solutions such as alginates and pectins undergo gelation in response to divalent cations or other such factors. Other carbohydrates such as agarose solutions are liquid at slightly elevated temperatures but gel at body temperatures. Polymerizable protein solutions are also very effective. These range from simple gelatin solutions that harden in response to a temperature reduction to fibrin/fibrinogen solutions that harden due to an enzymatic conversion. Hydrophilic organic polymers (many being acrylamide derivatives) are known that gel or harden in response to a temperature increase. It is possible to inject such polymers in their liquid form below body temperature and have them gel as they reach body temperature. These materials pose advantages over monomeric acrylamide because they are essentially non-toxic. The ideal inflation fluid "hardens" to provide support for the device but remains sufficiently flexible to adjust to bending or shortening of the aneurysm with age.

Figure 3:
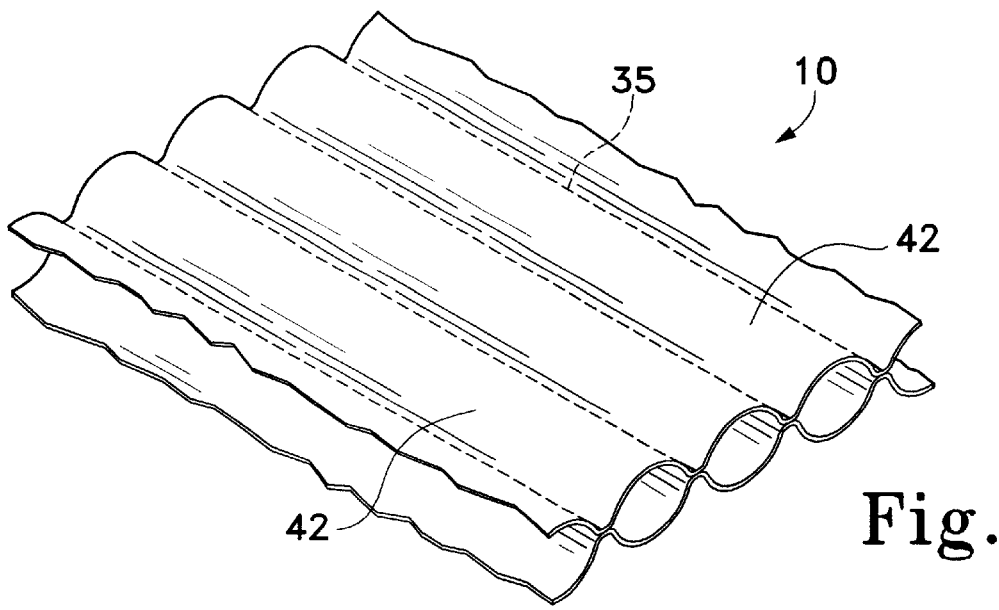
FIG. 3 shows a perspective view of a second embodiment of the device wherein the inflation space is subdivided into a plurality of longitudinally oriented compartments.
Figure 4:
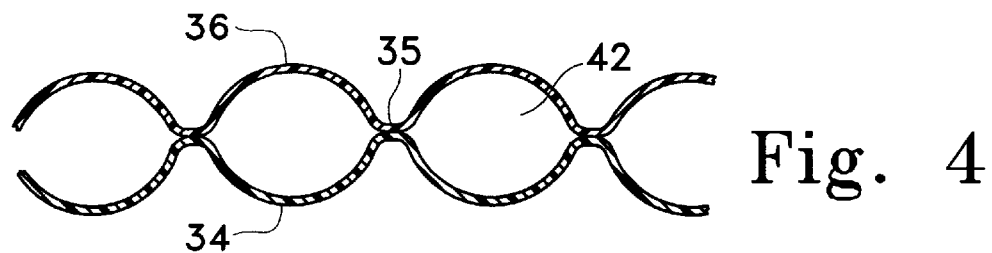
FIG. 4 shows a close up view of the regions of connection in the device of FIG. 3.

The simplest embodiment of the device 10 has connections 35 between the inner 34 and outer walls 36 only at the distal and proximal ends. However, there are a number of advantages to embodiments that bear additional connections. FIG. 3 shows a perspective view of a portion of the main body 12 of a device having a plurality of longitudinal connections 35 (in phantom) that divide the inflation space 32 into a plurality of longitudinal compartments 42. Such a structure can provide an improved device with improved resistance to longitudinal compression particularly where the inflation fluid used does not gel or polymerize. FIG. 4 is a cross-section of a portion of the device of FIG. 3 and shows that the connection 35 (the regions where the inner wall 34 is connected or fused to the outer wall 36) can be made relatively broad. If ePTFE materials with proper characteristics, such as internodal distances greater than about 30 μm, are used microcapillaries can penetrate these regions so that improved healing can occur and an intima can develop within the lumen 14 of the device 10. This is probably most important near the proximal and distal ends of the device which will be in contact with relatively healthy vessel walls from which such capillaries can grow. In the more central portions of the device 10 (the parts actually bridging the aneurysm) it is likely that thrombus will exist between the aneurysm walls and the device 10, thereby blocking infiltration of capillaries. The proximal and distal healing is important not only because it supports the formation of intima (which helps prevent thrombus formation) but also because the healing response firmly anchors the ends of the device 10 and prevents shifting thereof. Many prior art devices are forced to provide cumbersome anchoring barbs to prevent device movement.

Figure 5:
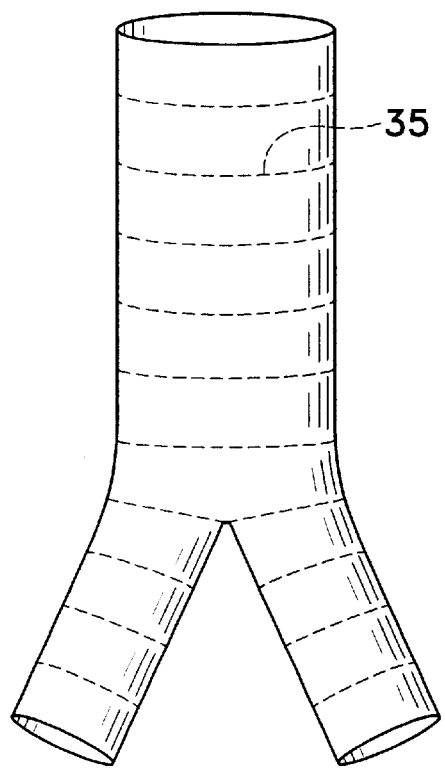
FIG. 5 shows circumferential regions of connection.
Figure 6:
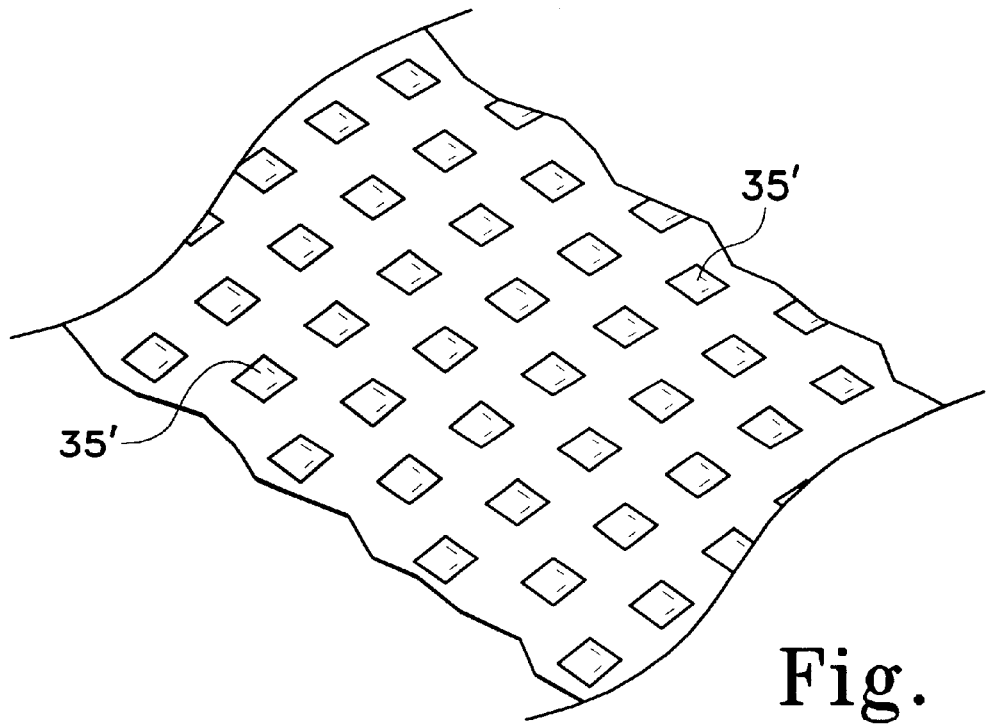
FIG. 6 shows punctate regions of connection.
Figure 7:
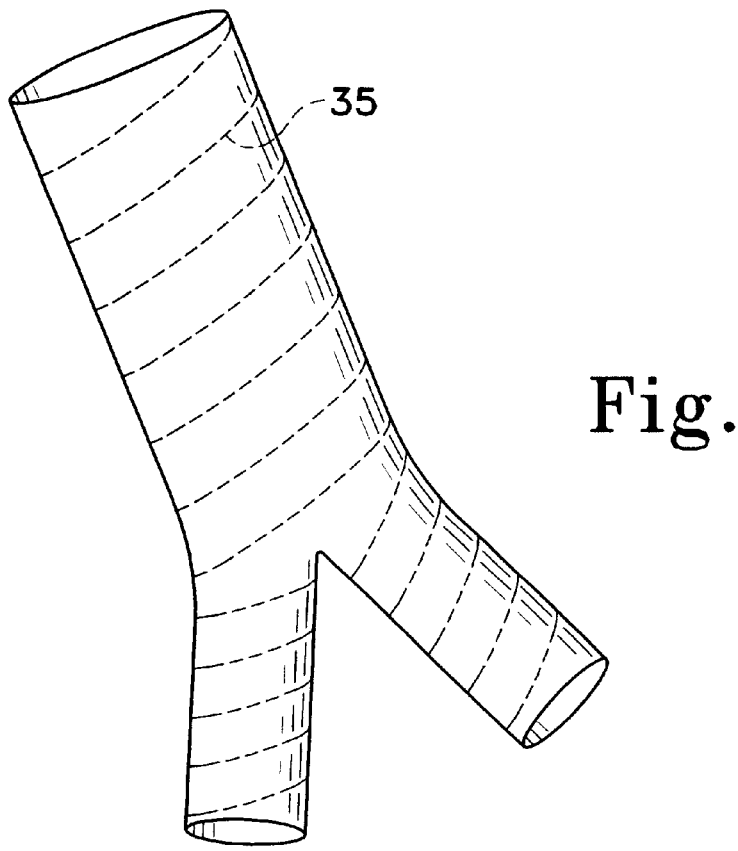
FIG. 7 shows a perspective view of a third embodiment of the device wherein the inflation space is subdivided by helically arranged region of connection.

Many other patterns of connections 35 are functional and may be advantageous. For healing purposes the connections 35 can comprise an elongated circumferentially arranged region as shown in FIG. 5. FIG. 6 shows a close up view of a portion of the surface of a version of the device 10 with a plurality of punctate connections 35' with various shapes for each individual region (e.g., rectangular or round). The punctate connections 35' can be arranged in a variety of patterns. As mentioned above, arrangement of the connections 35 to subdivide the inflation space 32 into longitudinal compartments provides a device having certain physical properties. FIG. 7 shows a perspective view of a device having connections 35 helically arranged. Either one connection 35 can spiral the entire length of the main body 12 or a plurality of connections 35 can be spirally arranged. This arrangement of connections 35 tends to produce a device 10 that is more flexible laterally (side to side) than the alternative embodiment having longitudinally oriented connections 35. It should be clear to one of skill in the art that the connections 35 that partition the inflation space 32 cannot continue from end to end of the device 10 because inflation fluid would be unable to flow from the inflation conduit 38 into all of the compartments 42. Rather, there must be interruptions in the connections 35 to allow inflation of all the compartments 42.

Figure 8:
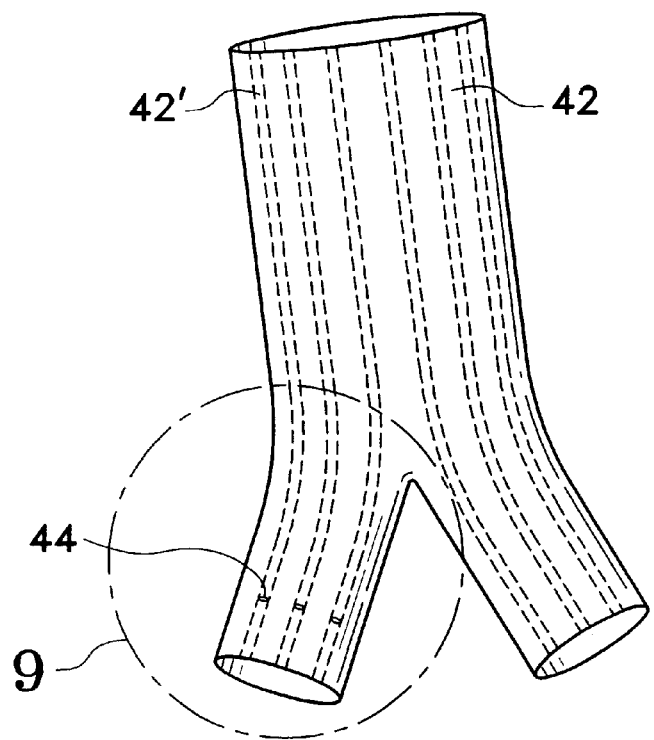
FIG. 8 shows a perspective view of a fourth embodiment of the device wherein the inflation space is separated into longitudinal compartments some of which are isolated from the inflation space for the insertion of supporting structures.

FIG. 8 shows a perspective version of a fourth embodiment of the present invention wherein the inflation space 32 is divided into a plurality of longitudinal compartments 42 by connections 35 between the inner 34 and outer 36 walls. Careful inspection will show that some of the compartments 42' are completely cut off from the inflation space 32. These compartments are in communication with the outside milieu through apertures 44. The purpose of the apertures 44 and the cut off compartments 42' is to permit the insertion of stiffening devices 46 after the device 10 has been inserted and inflated. This process can be likened to the insertion of fiberglass rods into pockets in a backpacking tent. This allows a backpacking tent to be compressed to a minimal size for transit. After the tent is unfolded, the rods are inserted to hold the tent in an open expanded state. Alternatively, the device 10 can be expanded by an external force, e.g., expanded by a separate balloon, and the stiffening devices 46 inserted.

Figure 9:
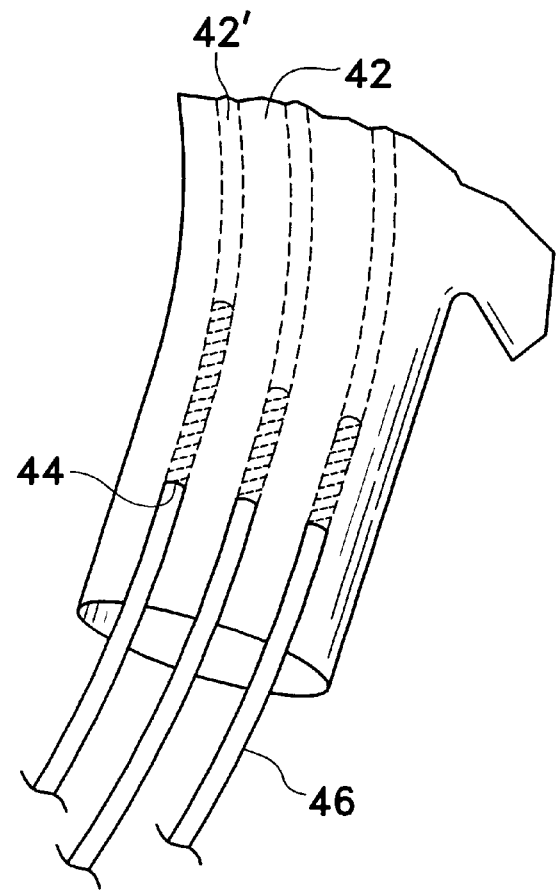
FIG. 9 shows the device of FIG. 8 with stiffening devices (phantom) partially inserted.

FIG. 9 shows the stiffening devices 46 partially inserted (shown in phantom). The stiffening devices 46 for all practical purposes behave like a stent. However, as noted above, inclusion of a stent in a graft significantly increases the profile of the graft in its compressed state. With the current invention the graft lacks a permanent stent so that it can be maximally compressed. After the device 10 is properly placed in an aneurysm, it is inflated to its full size by means of inflation fluid injected through the inflation conduit 38 (or otherwise expanded). Then the resilient stiffening devices 46 are inserted into the compartments 42' to provide improved strength and spring to the expanded device. The final physical properties of the expanded device are a combination between the properties of the inflation fluid (if used) and the stiffening devices 46. The illustrated example shows longitudinally oriented stiffening devices 46, but other orientations such as helical are possible.

To recap, the compressed device 10 is inserted into the aneurysm e.g., by means of a catheter threaded through an iliac artery. The device 10 resides in the tip of the catheter, and a pre-attached inflation conduit 38 can advantageously lead back though the catheter and be available at the entry site where the catheter is inserted into the patient. When the catheter tip is located in the AAA, the catheter is manipulated to release the compressed device 10. At that point the catheter can be slightly backed out to leave the AAA free for expansion of the device 10. Inflation fluid is pumped into the device 10 through the inflation conduit 38 thereby filling the inflation space 32 and causing the device 10 to assume its expanded shape. As this happens, the device can be pulled slightly toward the iliac artery through which the catheter was inserted either by means of the conduit 38 or a guide wire. This causes the proximal end (in terms of the entry site) of the iliac limb 16 to come into contact with the walls of the iliac artery below the aneurysm. The iliac opening 26 is sealed to the wall of and becomes continuous with the iliac artery to allow blood flow therethrough. As the device 10 completes its inflation, the contralateral limb 18 finds its way into the contralateral iliac artery and also becomes sealed into place. After inflation the inflation conduit 38 is preferably detached and withdrawn through the catheter. If a "hardening" inflation fluid is employed, the conduit 38 can advantageously be detached after hardening occurs thus obviating the need for valves to avoid fluid leakage.

If the device 10 is an embodiment with compartments 42' for insertion of stiffening devices, the stiffening devices 46 can be advanced, for example, from the insertion catheter by methods known to those of skill in the art. They are threaded through the apertures 44 to extend into the main body 12 where they add a centrifugal force that aids in sealing the wall around the distal opening 24 into contact with the aorta wall. It is also possible to configure the device 10 so that the stiffening devices 46 can be passed posteriorly from a more anterior region of the patient to enter the device through apertures 44 placed near the distal opening 24. An advantage of this alternative approach is that the stiffening devices 46 can more readily be extended into both iliac limbs 16, 18. However, this approach does involve using an additional incision and entry point. Again, stiffening devices 46 can be inserted into a device 10 expanded by alternative expansion means as opposed to inflation.

The device described above can be produced by methods well known to those of skill in the art of ePTFE fabrication. Each wall 34, 36 of the main body 12 can advantageously be fabricated by extrusion followed by expansion. The outer wall 36 component is then placed over the inner wall 34 component, e.g., on a mandrel. The connections 35 can be attained by several methods. A preferred method is to directly laminate the walls together by applying heat and pressure. This method is especially useful for production of connections 35 intended for promoting penetration of microcapillaries since lamination substantially leaves the ePTFE microstructure intact. Alternatively, any of a number of adhesives can be used to connect the PTFE layers. Thermoplastic materials such as polyethylene can be used since these materials when heated between the ePTFE layers will melt and interpenetrate the porous ePTFE to "glue" the layers together.

The iliac limbs 16, 18 can be formed as separate tubular extrudates and then glued or stitched to the main body 12. Generally a separate bifurcated inner structure and outer structure will be made, and then placed one over the other for the adhesion or lamination process that forms the connections 35. Alternately the bifurcation can be formed as a unitary structure by deforming the main body tubular extrudate over a special mandrel that has a bifurcation (e.g., two legs at one end rather like a human torso with legs). Essentially, the tubular extrudate is radially expanded to encompass both legs of the bifurcation. Then the material between the legs is laminated and then cut away leaving the legs of the mandrel surrounded by ePTFE with seams on the inner leg surfaces where they face each other.

In addition to the equivalents of the claimed elements, obvious substitutions now or later known to one with ordinary skill in the art are defined to be within the scope of the defined elements. The claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just described preferred embodiment can be configured without departing from the scope of the invention. The illustrated embodiments have been set forth only for the purposes of example and that should not be taken as limiting the invention. Therefore, it is to be understood that, within the scope of the appended claims, the invention may be practiced other than as specifically described herein.

What is claimed is:

1. A prosthetic device for endovascular repair of an aneurysm comprising:
   a first expanded polytetrafluoroethylene tubular member;
   a second expanded polytetrafluoroethylene tubular member coaxial with and of a diameter larger than a diameter of said first tubular member so that a space is formed therebetween, said first and second tubular members sealingly attached at proximal and distal ends, thereof, wherein said tubular members are bifurcated into tubular iliac limbs at said distal end; and
   port means for injection of an inflating fluid into the space between said tubular members.

2. A prosthetic device for endovascular repair of an aneurysm comprising:
   a first expanded polytetrafluoroethylene tubular member;
   a second expanded polytetrafluoroethylene tubular member coaxial with and of a diameter larger than a diameter of said first tubular member so that a space is formed therebetween, said first and second tubular members sealingly attached at proximal and distal ends, thereof; and
   port means for injection of an inflating fluid into the space between said tubular members, wherein said port means includes an inflation conduit and a valve mechanism, wherein said inflation conduit is removably attached to said tubular members.

3. A prosthetic device for endovascular repair of an aneurysm comprising:
   a first expanded polytetrafluoroethylene tubular member;
   a second expanded polytetrafluoroethylene tubular member coaxial with and of a diameter larger than a diameter of said first tubular member so that a space is formed therebetween, said first and second tubular members sealingly attached at proximal and distal ends, thereof;
   port means for injection of an inflating fluid into the space between said tubular members; and
   a plurality of contact points crossing the space, said contacts points formed by said first tubular member being laminated directly to said second tubular member, wherein said contact points are arranged circumferentially.

4. A prosthetic device for endovascular repair of an aneurysm comprising:
   a first expanded polytetrafluoroethylene tubular member;
   a second expanded polytetrafluoroethylene tubular member coaxial with and of a diameter larger than a diameter of said first tubular member so that a space is formed therebetween, said first and second tubular members sealingly attached at proximal and distal ends, thereof;
   port means for injection of an inflating fluid into the space between said tubular members; and
   a plurality of contact points crossing the space, said contacts points formed by said first tubular member being laminated directly to said second tubular member, wherein said contact points are arranged helically.

5. A prosthetic device for endovascular repair of an aneurysm comprising:
   an expanded polytetrafluoroethylene component comprising:
      a first expanded polytetrafluoroethylene tubular member;
      a second expanded polytetrafluoroethylene tubular member coaxial with and of a diameter larger than a diameter of said first tubular member so that a space is formed therebetween, said first and second tubular members sealingly attached at proximal and distal ends, thereof;
      port means for injection of an inflating fluid into the space between said tubular members; and
      a plurality of longitudinally oriented chambers disposed between said first tubular member and said second tubular member and separated from the space formed by a plurality of laminations between said first tubular member and said second tubular member; and
      a plurality of stiffening members inserted into said chambers after the inflating fluid has been injected into the space.

6. The prosthetic device according to claim 5, wherein said expanded polytetrafluoroethylene component is bifurcated into tubular iliac limbs at said distal end.

7. The prosthetic device according to claim 5, wherein said port means includes an inflation conduit and a valve mechanism, wherein said inflation conduit is removably attached to said expanded polytetrafluoroethylene component.

8. A method for inserting the prosthetic device of claim 5 into an aneurysm comprising the steps of:
   compressing the expanded polytetrafluoroethylene component;
   placing the compressed component into a catheter;

using the catheter to endovascularly insert said compressed component into an aneurysm;

inflating the compressed component by injecting inflating fluid through the port means; and inserting the stiffening members into the chambers.

9. A prosthetic device for endovascular repair of an aneurysm comprising:

a first tubular member;

a second tubular member coaxial with and of a diameter larger than a diameter of said first tubular member so that a space is formed therebetween, said first and second tubular members sealingly attached at proximal and distal ends, thereof; and a plurality of chambers disposed between said first tubular member and said second tubular member and formed from the space by a plurality of laminations between said first tubular member and said second tubular member, said chambers sized and structured for insertion of stiffening members after said device is placed into an aneurysm.

10. A method for inserting the prosthetic device of claim 9 into an aneurysm comprising the steps of:

compressing the device;

placing the compressed device into a catheter;

using the catheter to endovascularly insert said compressed device into an aneurysm;

expanding the compressed device within the aneurysm; and inserting the stiffening members into the chambers.

* * * * *